(12) United States Patent
Gladden Md Facc

(10) Patent No.: US 12,306,609 B2
(45) Date of Patent: May 20, 2025

(54) APPARATUS FOR PRINTING ENERGY BALANCE FORMULATION AND A METHOD FOR ITS USE

(71) Applicant: Oceandrive Ventures, LLC, Rio Grande, PR (US)

(72) Inventor: Jeffrey Gladden Md Facc, Rio Grande, OR (US)

( * ) Notice: Subject to any disclaimer, the term of this patent is extended or adjusted under 35 U.S.C. 154(b) by 0 days.

(21) Appl. No.: 18/398,634

(22) Filed: Dec. 28, 2023

(65) Prior Publication Data

US 2024/0126232 A1   Apr. 18, 2024

Related U.S. Application Data

(63) Continuation of application No. 17/952,668, filed on Sep. 26, 2022, now Pat. No. 11,899,425.

(51) Int. Cl.
*G05B 19/408* (2006.01)
*B33Y 50/00* (2015.01)

(52) U.S. Cl.
CPC .......... *G05B 19/4083* (2013.01); *B33Y 50/00* (2014.12); *G05B 2219/34082* (2013.01); *G05B 2219/49023* (2013.01)

(58) Field of Classification Search
CPC ...... G05B 19/4083; G05B 2219/34082; G05B 2219/49023; B33Y 50/00; G16H 50/20; G16H 20/10
(Continued)

(56) References Cited

U.S. PATENT DOCUMENTS 7,937,139 B2 *  5/2011  Horne ................... A61B 5/411
                                                600/548
8,332,027 B2 * 12/2012  Larsen ................ A61H 39/002
                                                600/548
(Continued)

FOREIGN PATENT DOCUMENTS

CN     109346175 A     2/2019
CN     111584041 A     8/2020
(Continued)

OTHER PUBLICATIONS

Breiner Whole-Body Health Center, EAV Testing, Youtube video, https://www.youtube.com/watch?v=1RMsh10ync0.

*Primary Examiner* — Thomas C Lee
*Assistant Examiner* — Michael Tang
(74) *Attorney, Agent, or Firm* — Caldwell Intellectual Property Law

(57) ABSTRACT

An apparatus for printing an energy balance formulation, wherein the apparatus includes at least a processor and a memory communicatively connected to the at least a processor, the memory containing instructions configuring the at least a processor to receive an energy quantifier related to a user and generate an energy rebalancing plan wherein the energy rebalancing plan identifies an energy balance formulation includes training a machine-learning process using energy training data, wherein the energy training data contains a plurality of inputs containing energy quantifiers correlated to a plurality of outputs containing energy rebalancing plans. The memory contains instructions further configuring the processor to generate the energy rebalancing plan as a function of the machine-learning process and the energy quantifier. The memory contains instructions further configuring the additive manufacturing device to print the
(Continued)

energy balance formulation based on the energy rebalancing plan.

16 Claims, 7 Drawing Sheets

(58) Field of Classification Search
USPC .......................................................... 700/119
See application file for complete search history.

(56) References Cited

U.S. PATENT DOCUMENTS

| | | |
|---|---|---|
| 2010/0298863 A1 | 11/2010 | Hindinger |
| 2017/0372016 A1 | 12/2017 | Jiang |
| 2021/0205228 A1* | 7/2021 | Huang .................... B33Y 80/00 |
| 2022/0062621 A1* | 3/2022 | Hogg .................... A61N 1/0456 |
| 2023/0086217 A1* | 3/2023 | Hajij ......................... G06N 3/08 |
| | | 705/3 |

FOREIGN PATENT DOCUMENTS

| | | | | |
|---|---|---|---|---|
| CN | 112336351 A | * | 2/2021 | |
| WO | WO-2020190332 A1 | * | 9/2020 | ........... A61B 5/0532 |

* cited by examiner

APPARATUS FOR PRINTING ENERGY BALANCE FORMULATION AND A METHOD FOR ITS USE

CROSS-REFERENCE TO RELATED APPLICATIONS

This application is a continuation of Non-provisional application Ser. No. 17/952,668, filed on Sep. 26, 2022, and entitled "AN APPARATUS FOR PRINTING ENERGY BALANCE FORMULATION AND A METHOD FOR ITS USE," the entirety of which is incorporated herein by reference.

FIELD OF THE INVENTION

The present invention generally relates to the field of printing. In particular, the present invention is directed to an apparatus for printing an energy balance formulation and a method for its use.

BACKGROUND

Manufacturing formulations using rapid prototyping have thus far been inadequate to the task of producing complex and effective formulation for patients to improve and balance their energy.

SUMMARY OF THE DISCLOSURE

In an aspect, a printer for printing an energy balance formulation includes at least a processor and a memory communicatively connected to the at least a processor, the memory contains instructions configuring the at least a processor to receive an energy quantifier related to a user, wherein receiving the energy quantifier includes obtaining a baseline energy meridian assessment in a specific interval, identify one or more body areas with insufficient life energy of the user as a function of the energy quantifier, generate an energy rebalancing plan a function of the energy quantifier, wherein generating the energy rebalancing plans includes identifying an energy balance formulation, identifying a quantity of one or more ingredients in the energy balance formulation and determining a probability of side effects based on the one or more ingredients of the energy balance formulation and print the energy balance formulation based on the energy rebalancing plan using an additive manufacturing process, wherein printing the energy balance formulation includes transmitting the energy balance formulation to the one or more body areas with insufficient life energy of the user.

In another aspect, a method for printing an energy balance formulation includes receiving, using at least a processor, an energy quantifier related to a user, wherein receiving the energy quantifier includes obtaining a baseline energy meridian assessment in a specific interval, identifying, using the at least a processor, one or more body areas with insufficient life energy of the user as a function of the energy quantifier, generating, using the at least a processor, an energy rebalancing plan a function of the energy quantifier, wherein generating the energy rebalancing plans includes identifying an energy balance formulation, identifying a quantity of one or more ingredients in the energy balance formulation and determining a probability of side effects based on the one or more ingredients of the energy balance formulation and printing, using the at least a processor, the energy balance formulation based on the energy rebalancing plan using an additive manufacturing process, wherein printing the energy balance formulation includes transmitting the energy balance formulation to the one or more body areas with insufficient life energy of the user.

These and other aspects and features of non-limiting embodiments of the present invention will become apparent to those skilled in the art upon review of the following description of specific non-limiting embodiments of the invention in conjunction with the accompanying drawings.

For the purpose of illustrating the invention, the drawings show aspects of one or more embodiments of the invention. However, it should be understood that the present invention is not limited to the precise arrangements and instrumentalities shown in the drawings, wherein.

Figure 3:
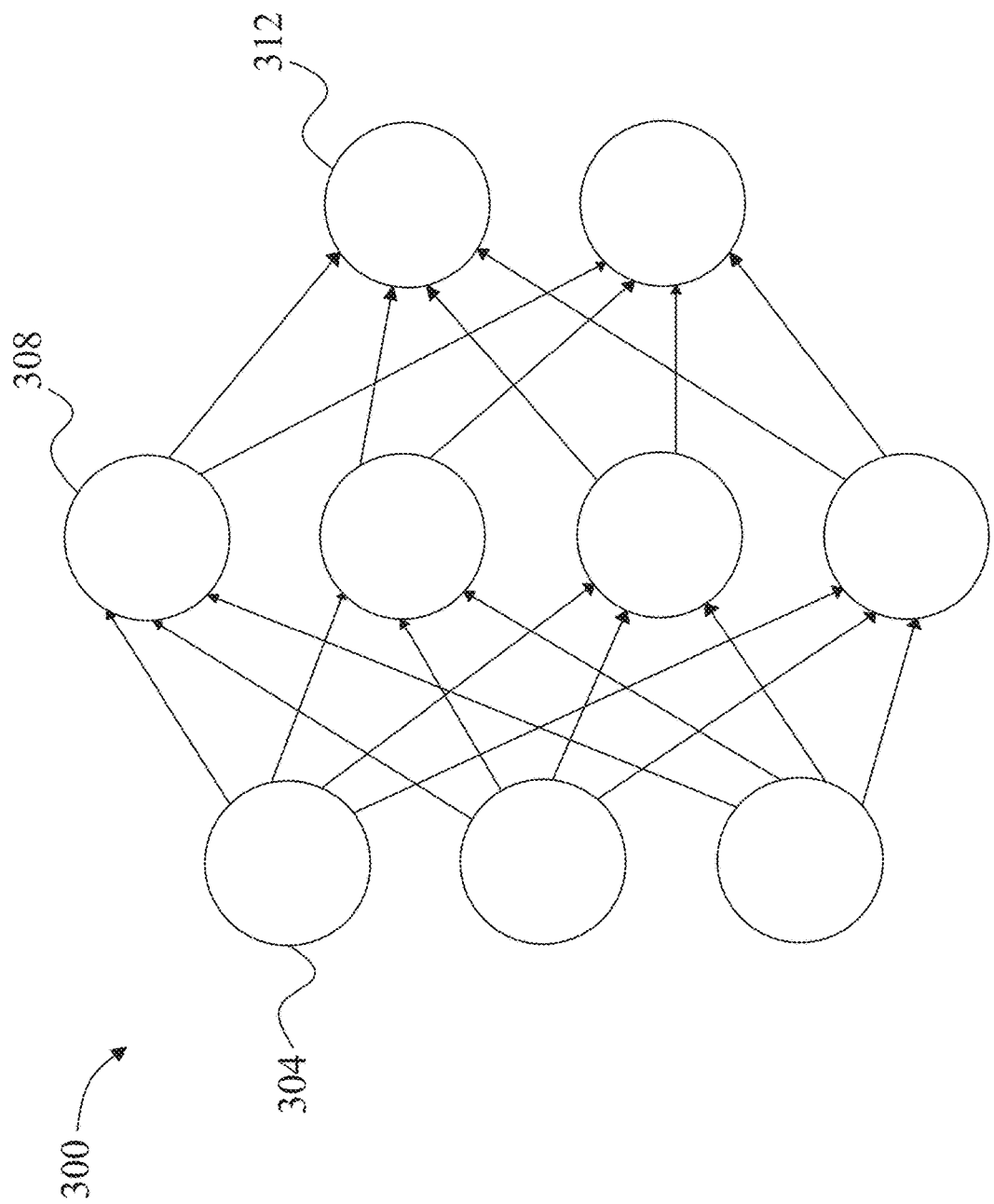
Figure 4:
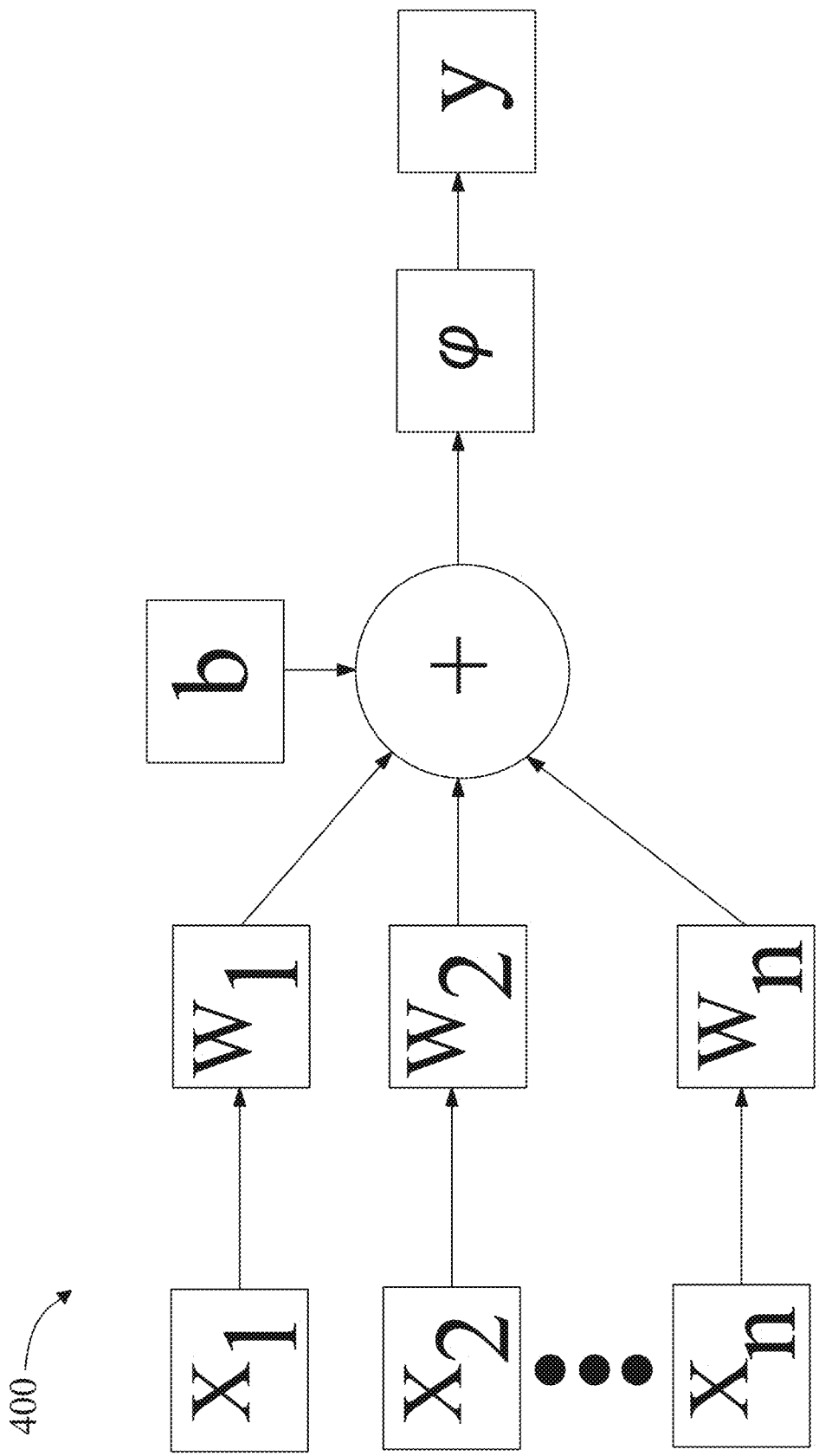
Figure 5:
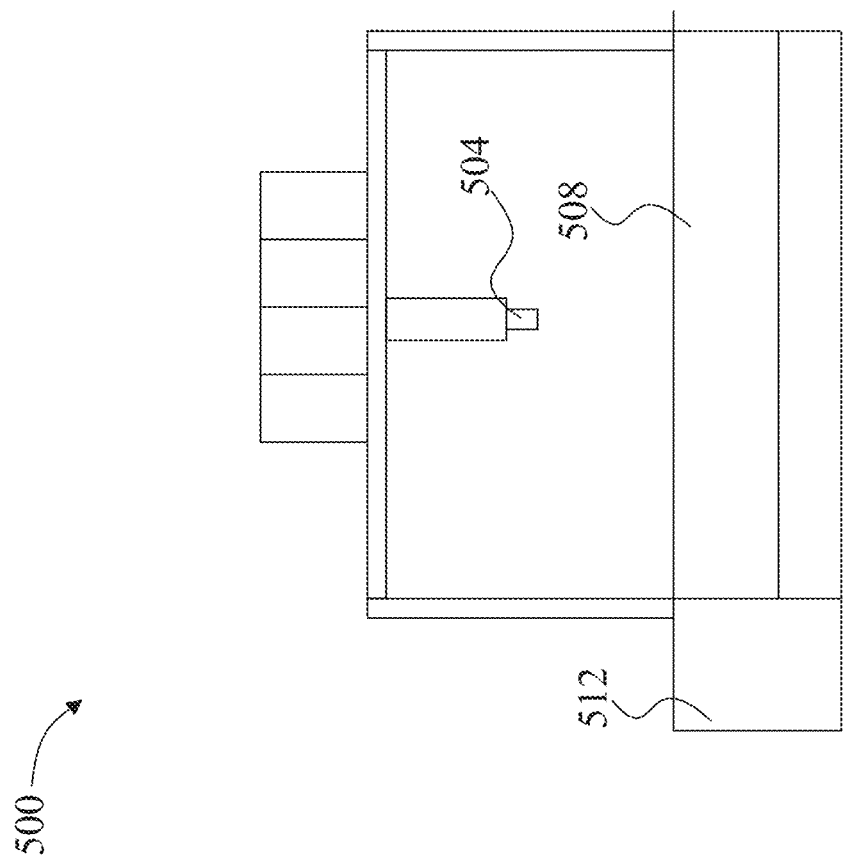
Figure 6:
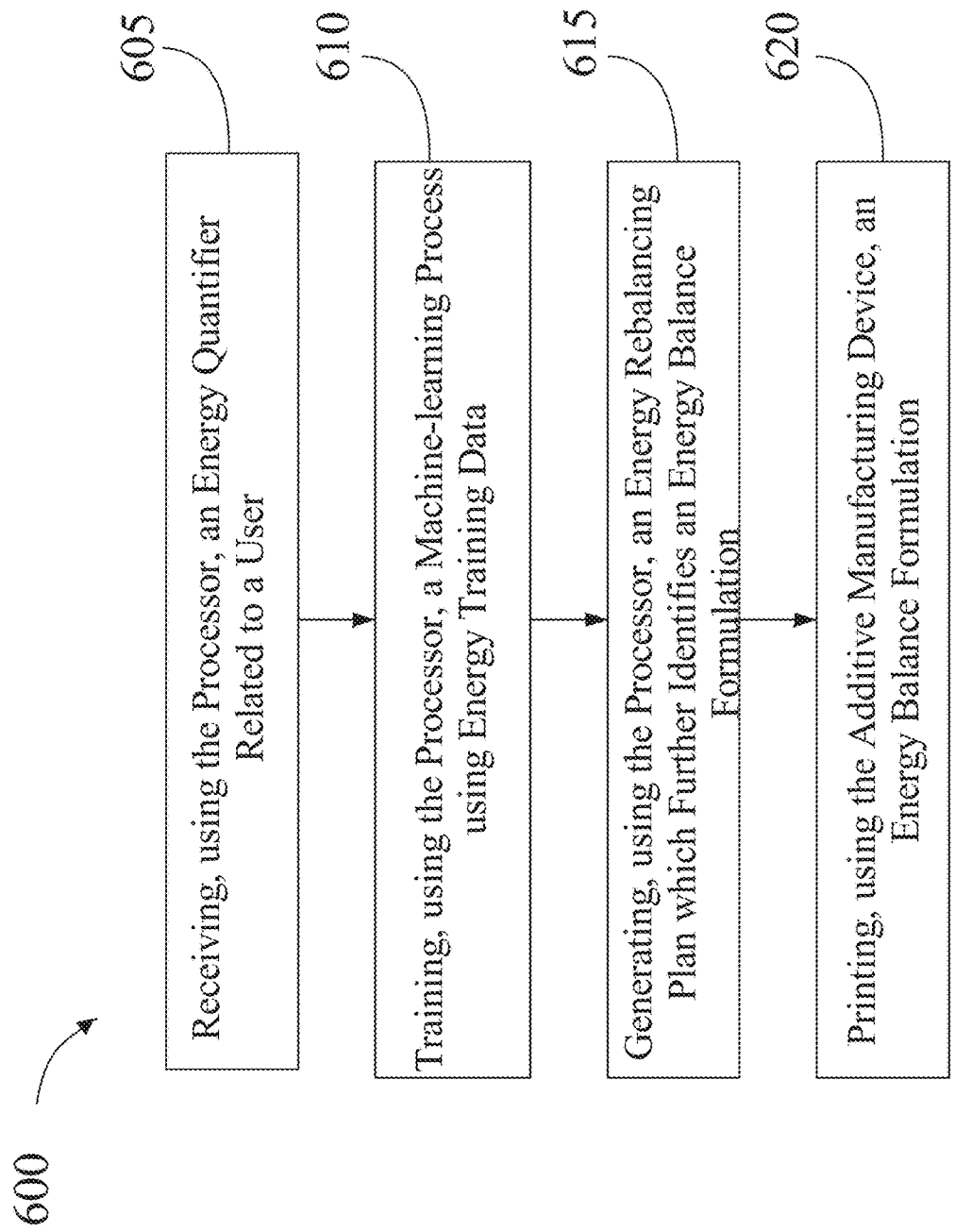
Figure 7:
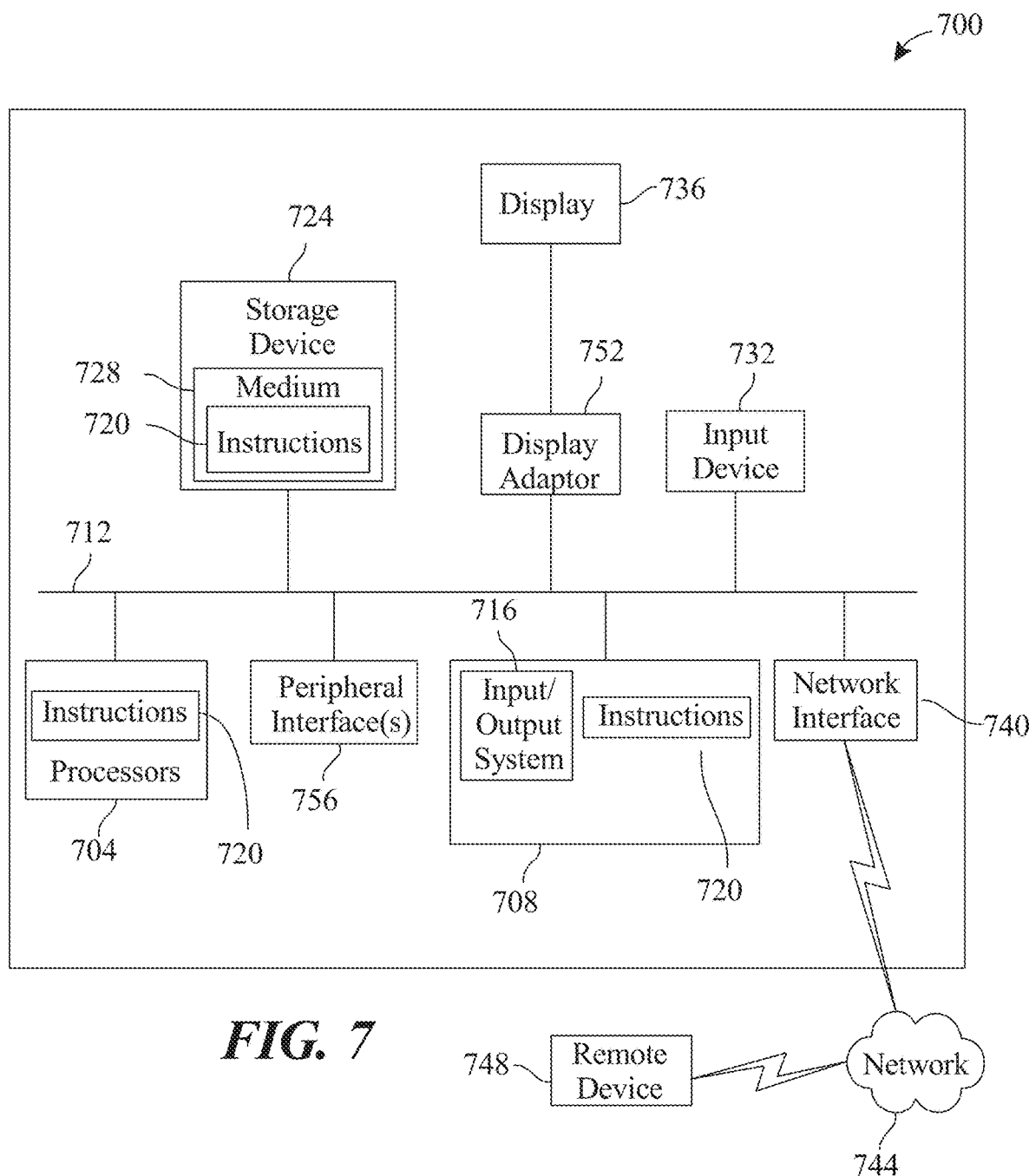

FIG. 3 a diagram of an exemplary embodiment of neural network;

FIG. 4 a diagram of an exemplary embodiment of a node of a neural network;

FIG. 5 is a schematic diagram of an exemplary embodiment of an additive manufacturing device;

FIG. 6 is a flow diagram of an exemplary embodiment of a method of printing energy balance formulation; and FIG. 7 is a block diagram of a computing system that can be used to implement any one or more of the methodologies disclosed herein and any one or more portions thereof.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for printing energy balance formulation. The printer may comprise at least a processor, a memory and an additive manufacturing device communicatively connected to the processor. The processor may further be configured to receive an energy quantifier related to a user. The processor then may generate an energy rebalancing plan wherein the energy rebalancing plan identifies an energy balance formulation includes training a machine-learning process using energy training data, wherein the energy training data contains a plurality of inputs containing energy quantifiers correlated to a plurality of outputs containing energy rebalancing plans. The energy rebalancing plan may then be generated as a function of the machine-learning process and the energy quantifier. The additive manufacturing device then prints the energy balance formulation based on the energy rebalancing plan. Exemplary embodiments illustrating aspects of the present disclosure are described below in the context of several specific examples.

Figure 1:
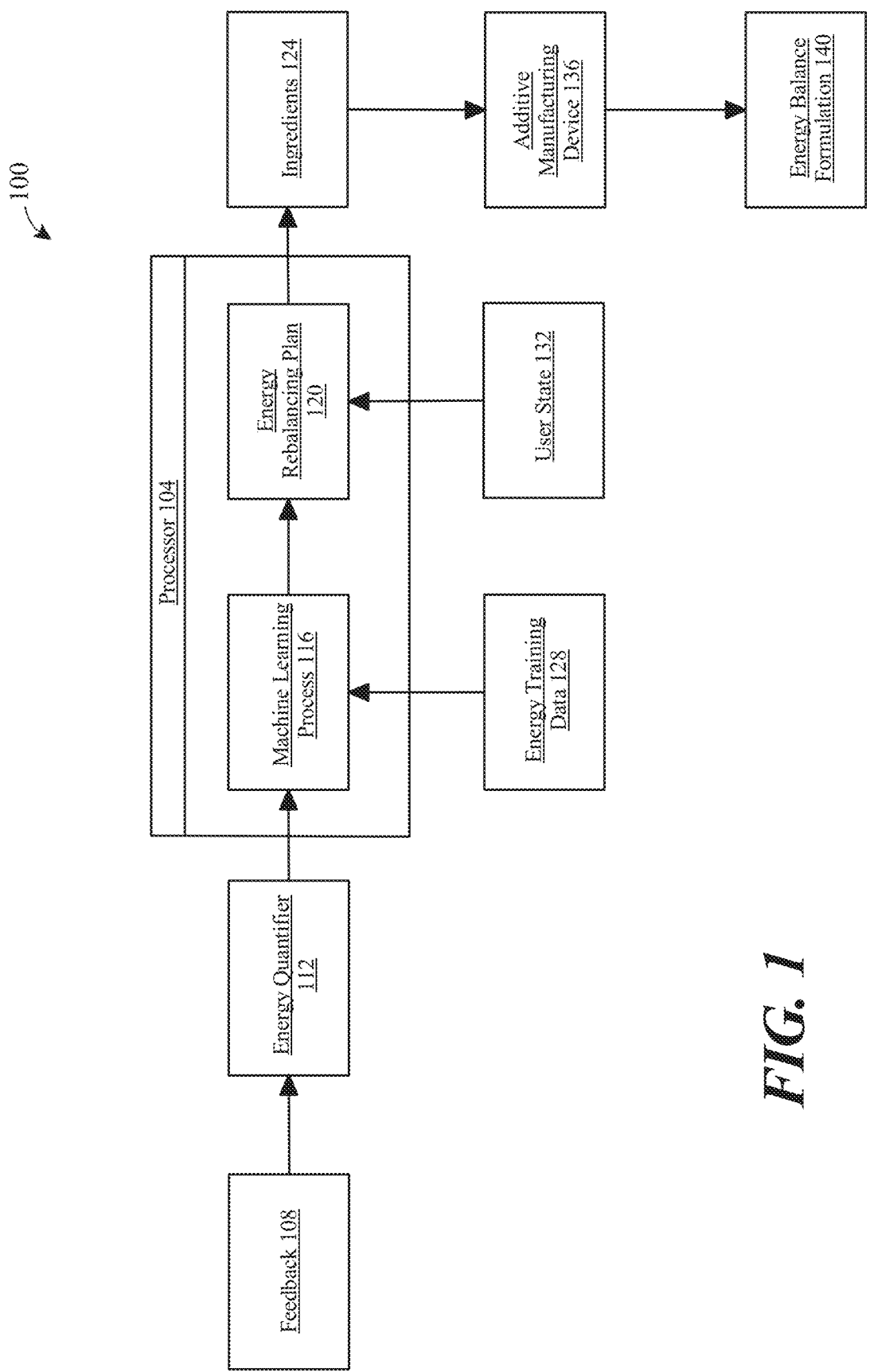
FIG. 1 is a block diagram of an exemplary embodiment of an apparatus for printing energy balance formulation.

Referring now to FIG. 1, an exemplary embodiment of an apparatus 100 for printing an energy balance formulation is illustrated. Apparatus may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Apparatus may include a single computing device operating independently, or may include two or more computing device operating in concert, in parallel, sequentially or the like; two or more computing devices may be included together in a single computing device or in two or more computing devices. Apparatus may interface or communicate with one or more additional devices as described below in further detail via a network interface device. Network interface device may be utilized for connecting Apparatus to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus may include but is not limited to, for example, a computing device or cluster of computing devices in a first location and a second computing device or cluster of computing devices in a second location. Apparatus may include one or more computing devices dedicated to data storage, security, distribution of traffic for load balancing, and the like. Apparatus may distribute one or more computing tasks as described below across a plurality of computing devices of computing device, which may operate in parallel, in series, redundantly, or in any other manner used for distribution of tasks or memory between computing devices. Apparatus may be implemented using a "shared nothing" architecture in which data is cached at the worker, in an embodiment, this may enable scalability of system 100 and/or computing device.

With continued reference to FIG. 1, apparatus 100 may be designed and/or configured to perform any method, method step, or sequence of method steps in any embodiment described in this disclosure, in any order and with any degree of repetition. For instance, Apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, The processor 104 may receive, from a user, an energy quantifier 112 related to the user. As used in this disclosure, "receive" from a user means accepting, collecting, or otherwise receiving input from a user and/or device. As described herein, an "energy quantifier" is a numeric measurement used to represent, measure, calculate, monitor, experiment, and/or evaluate the amount or level of the life energy flowing inside the energy meridian of a human or life body. An energy quantifier may be measured and/or derived by evaluation of telomeres, mitochondria, proteomic measures and/or evaluations, glycans measures and/or evaluations, oncogenic measures and/or evaluations, determinations of epigenetic rates of aging, epigenetic urine measures and/or evaluations, DNA repair measures and/or evaluations, epigenetic intrinsic measures and/or evaluations, epigenetic extrinsic measures and/or evaluations, mTor AMPK balance measures and/or evaluations, NAD measures and/or evaluations, NADH measures and/or evaluations, determinations regarding prevalence, health or other qualities of stem cells, senescent cell burden measures and/or evaluations, senescent cell SASP measures and/or evaluations, immune system measures and/or evaluations, and/or inflammation measures and/or evaluations. An energy quantifier 112 may be measured by examining real time feedback 108 by sending electric impulses with different frequency into the user. In some embodiments, an energy quantifier 112 may be used to locate one or more external or internal area, or one or more energy meridians of a human or life body, where contains excessive, moderate, or insufficient life energy. An energy quantifier 112 may also be used to detect disorganized, misaligned, atrophied, or necrotic energy meridians of a human or life body.

With continued reference to FIG. 1, in an embodiment, receiving energy quantifier 112 related to the user through processor 104 of apparatus 100 may further include, obtaining a baseline energy meridian assessment related to the user and generate an energy quantifier 112 as a function of the baseline energy meridian assessment. As used in this disclosure, a "baseline energy meridian assessment" is an evaluation on one or more energy meridian of the user. In some cases, real time feedback 108 may include baseline energy meridian assessment. In some embodiments, baseline energy meridian assessment may include a plurality of questions, answered by the user, which may include, but is not limited to, emotions, mental health status, activities, risks, lifestyle choices, and the like of the user thereof. In some cases, the plurality of questions of baseline energy meridian assessment may include questions generated based on the user's medical and/or health records. In a non-limiting example, baseline energy meridian assessment may include a plurality of questions examining how often a user feels loved. In another example, baseline energy meridian assessment may include a plurality of questions examining how frequently a user felt joy in the past week. In other embodiments, baseline energy meridian assessment may also include a set of actions, performed by the user, which may include, but is not limited to, walking, running, squatting, jumping, lifting, sleeping, eating, thinking, leaning, and the like. For instance, baseline energy meridian assessment may ask user to perform one or more predetermined tasks such as lifting left leg, and/or completing a squat, and/or jumping to certain distance above the ground, and/or the like. In some cases, baseline energy meridian assessment may be completed initially, and repeated at a specified interval, wherein the specified interval may include, but is not limited to, hourly, daily, biweekly, weekly, bimonthly, monthly, yearly, and the like. In other cases, baseline energy meridian assessment may be obtained based on a previous baseline energy meridian assessment related to the user. For example, the user may be asked to complete baseline energy meridian assessment on the first day of each month.

With continued reference to FIG. 1, the energy quantifier 112 may include an energy meridian flow information. As described herein, an "energy meridian flow information" is information regarding energy meridians related to the user. As described herein, "information regarding energy meridians" is information describing, measuring, or otherwise characterizing a system and/or theorized system of hidden, blocked, or unobstructed channels or sub-channels, or pathways or sub-pathways where life energy flows inside a body of a human being or other organism. Information regarding energy meridians may correspond to information regarding, measurements of, and/or evaluations of a peripheral and/or central nervous system of a human being or other organism having a nervous system. Information regarding energy meridians may be used in procedures such as acupuncture, electroacupuncture, acupressure, moxibustion, cupping, massage and the like.

With continued reference to FIG. 1, the energy quantifier 112 may identify one or more body areas with insufficient life energy on the user. As described herein, an "area with insufficient life energy" is an area of a body of a human or other animal that has been characterized by a person or process as lacking a sufficient amount of life energy, where "life energy" is a measured or theorized form of energy related to one or more portions of a body of a human or other organism, such as without limitation a brain, lungs, liver, bladder, kidneys, heart, stomach, and/or intestines inside the body. In some embodiments, an identification of one or more body areas with insufficient life energy may also include and/or be performed using an evaluation of a mental health status of a human or other organism. This may include an evaluation of mental health of a human or other organism as it pertains to overall energy and/or sensation of energy, safety, wisdom, spiritual health, overall joy, relationship health, growth mindset, and overall mental health. Life energy as used in this context may include without limitation, Prana, Qi, Chi, life force energy, and/or vital energy. In an embodiment, an evaluation of and/or determination regarding life energy or human or life may encompass an evaluation from a mental health professional and/or active or passive user inputs. Furthermore, energy quantifier 112 may also identify one or more energy meridians as disorganized or misaligned in a body of user, for instance and without limitation as described above. In an embodiment, an energy quantifier 112 may identify a meridian pattern. As used in this disclosure, a "meridian pattern" is a particular system of meridians where life energy circulates.

With continued reference to FIG. 1, the Apparatus 100 may generate an energy rebalancing plan 120 as a function of the received energy quantifier 112. As described herein, an "energy rebalancing plan" is a list of ingredients, substances, and materials with corresponding instructions or descriptions that ameliorate the life energy distribution, relieve symptoms, and cure disease in human body. In some cases, ingredients, and/or substances, and/or materials within energy rebalancing plan 120 may include without a physical presence. For example, an electric current or a segment of sound. In a non-limiting example, energy rebalancing plan 120 may include a list of electric current, wherein each electric current in the list of electric current is at a specified frequency. In another example, energy rebalancing plan 120 may include a list of songs. Processor 104 may generate the energy rebalancing plan using machine-learning process trained with energy training data 128. The energy training data 128 is a plurality of data entries containing a plurality of inputs that are correlated to a plurality of outputs for training a processor by a machine-learning process to align, classify, and determine the energy rebalancing plan to/of the user. In an embodiment, the inputs of the energy training data may contain one or more energy quantifiers and the outputs of the energy training data may contain energy rebalancing plan. In an embodiment, the energy training data 128 may encompass an evaluation from a mental health professional and/or user inputs. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, the energy rebalancing plan 120 may further identify as an energy balance formulation 140. "Energy balance formulation," as used in this disclosure, is a liquid or solid composite produced using one or more ingredients according to the energy rebalancing plan 120 through additive manufacturing process using an additive manufacturing device 136. In an embodiment, the energy balance formulation may include a plurality of quantities of a plurality of ingredients. As used in this disclosure, an "additive manufacturing process" is a process in which material is added incrementally to a body of material in a series of two or more successive steps. A material may be added in the form of a stack of incremental layers; each layer may represent a cross-section of an object to be formed upon completion of an additive manufacturing process. Each cross-section may, as a non-limiting example be modeled on a processor as a cross-section of graphical or textural representation of the object to be formed. An "additive manufacturing device," as used in this disclosure, is a device that performs additive manufacturing processes. Deposition of material in additive manufacturing processes may be accomplished by any suitable means. Deposition may be accomplished using stereolithography, in which successive layers of polymer material are deposited and then caused to bind with previous layers using a curing process such as curing using ultraviolet light. Additive manufacturing processes may include "three-dimensional printing" processes that deposit successive layers of power and binder; the powder may include polymer or ceramic powder, and the binder may cause the powder to adhere, fuse, or otherwise join into a layer of material making up the body of material or product. Additive manufacturing may include metal three-dimensional printing techniques such as laser sintering including direct metal laser sintering (DMLS) or laser powder-bed fusion. Likewise, additive manufacturing may be accomplished by immersion in a solution that deposits layers of material on the body of material, by depositing and sintering materials having melting points such as metals, such as selective laser sintering, by applying fluid or paste-like materials in strips or sheets and then curing that material either by cooling, ultraviolet curing, and the like, any combination of the above methods, or any additional methods that involve depositing successive layers or other increments of material. Methods of additive manufacturing may include without limitation vat polymerization, material jetting, binder jetting, material extrusion, fuse deposition modeling, powder bed fusion, sheet lamination, and directed energy deposition. Methods of additive manufacturing may include adding material in increments of individual atoms, molecules, or other particles. An additive manufacturing process may use a single method of additive manufacturing or combine two or more methods.

With continued reference to FIG. 1, in some embodiments, determining the quantity of one or more ingredients (i.e., ingredients in combination) in the energy balance formulation may include, but not limited to, using a machine-learning process trained with the ingredient training data. The ingredient training data is a plurality of data entries containing a plurality of inputs that are correlated to a plurality of outputs for training a processor by a machine-learning process to align, classify, and determine the quality of one or more ingredients in the energy balance formulation. In an embodiment, the inputs of the ingredient training data may contain one or more ingredients or ingredient combinations and the outputs of the ingredient training data may contain one or more health and/or energy effects. In an embodiment, the ingredient training data may include data element that describe the interactions between ingredients. The interactions between ingredients may include negative interactions, positive interactions, or no interactions. For example, the negative interactions between two or more ingredients (or within an ingredients combination) are interactions that describes a tendency of one or more ingredients to decrease the effectiveness of other ingredients within the combination. The positive interaction between two or more ingredients (or within an ingredients combination) is an interaction describes a tendency of one or more ingredients to increase the effectiveness of other ingredients within the combination, and the no interaction between two or more ingredients (or within an ingredients combination) is an interaction describes a tendency of one or more ingredients have no effect on other ingredients within the combination. In an embodiment, determining the quantity of one or more ingredients or ingredients in combination in the energy balance plan may also include modification based on the previously determined quantities using the machine-learning process with ingredient training data as described above.

With continued reference to FIG. 1, the energy balance formulation 140 may also identify one or more side-effect and/or its corresponding probability based on the ingredient combination. As used in this disclosure, a "side-effect" is an unwanted or undesirable effects that are related to one or more ingredients or ingredients combination within the energy balance formulation. The side-effect may include, but is not limited to, diarrhea, dizziness, drowsiness, fatigue, heart issues, hives, nausea and vomiting, rash, stomach upset, fever, allergy, infection, pain, redness, swelling and the like. In an embodiment, generating the energy rebalancing plan or the energy balance formulation may further include identifying zero to more side-effect of the energy balance formulation. In another embodiment, identifying the side-effect of the energy balance formulation may include, but is not limited to, using a machine-learning process trained with side-effect training data. The side-effect training data is a plurality of data entries containing a plurality of inputs that are correlated to a plurality of outputs for training a processor by a machine-learning process to align, classify, and determine the side-effect of the energy balance formulation to/of the user. In an embodiment, the inputs of the side-effect training data may contain one or more ingredients or ingredients combination and the outputs of the side-effect training data may contain medical side-effects.

In some embodiment, the energy balance formulation may include a dosage schedule. The dosage schedule may include, but is not limited to hourly, daily, weekly, biweekly, monthly, bimonthly, yearly and the like. The dosage schedule may also include the amount of the energy balance formulation to take each time. In a non-limited example, the energy balance formulation may include a dosage schedule of one tablet per day, seven tablets per week. In an embodiment, identifying the dosage schedule may include using a machine-learning model trained with dosage schedule training data. The dosage schedule training data is a plurality of data entries containing a plurality of inputs that are correlated to a plurality of outputs for training a processor by a machine-learning process to align, classify, and determine the dosage schedule of the energy balance formulation to/of the user. In an embodiment, the inputs of the dosage schedule training data may contain one or more ingredients or ingredients combinations and side-effects, and the outputs of the dosage schedule training data may contain the dosage schedule.

With continued reference to FIG. 1, the energy balance formulation 140 may also be selected as a function of the user state 132. As described herein, a "user state" is textual or numerical parameter related to one or more feelings, emotions, and intentions of the user. In a non-limiting example, a user state 132 can be selected or input by the user as anger, hunger, fear, joy, love, sadness, surprise, fatigue, pain, stress, sleep, and the like. The energy balance formulation 140 may also be selected as a function of one or more target energy meridians identified by the energy rebalancing plan 120. In an embodiment, energy balance formulation 140 may include a subset of ingredients from plurality of ingredients 124 based on the energy rebalancing plan 120. In another embodiment, an energy balance formulation 140 may be applied, swallowed, or drunk by the user.

With continued reference on FIG. 1, the apparatus 100 may be configured to print, using the additive manufacturing device 136, the energy balance formulation 140. As used in this disclosure, "printing" means producing a material from scratch. In a non-limited example, material may be energy balance formulation 140. In some cases, material may be tangible. As used in this disclosure, "tangible" is used to describe material that is perceptible by touch. In an embodiment, printing energy balance formulation 140 may include printing energy balance formulation onto an H2 tablet. As described herein, an "H2 tablet" is a tablet with H2 molecular hydrogen added to it. In some embodiments, H2 tablet may be used to reduce the production of COX-2 in the body of the user, wherein COX-2 is enzyme that responsible for inflammation. In other embodiments, H2 tablet may be used to increase energy, slow down the aging process, and improve muscle recovery. In other cases, material may be intangible. As used in this disclosure, "intangible" is used to describe material that is unable to be touched and grasped. In some embodiment, printing energy balance formulation 140 may include printing energy balance formulation as an electric current, wherein the electric current may include an electric frequency. As used in this disclosure, an "electric current" is a stream of charged electrons as used in this disclosure, "electric frequency" is the measure of the rate of electric current oscillation. In some cases, electric current may include a plurality of electric frequencies. In an embodiment, each electric frequency within plurality of electric frequency may be different. In a non-limited example, manufacturing device 136 may print (in another word, transmit) energy balance formulation as an electric current with 0.5 milliampere (mA) at 30 Hertz (HZ). The electric current may be transmit into a body of the user, wherein the body of the user may be energy insufficient body area of the user. Further, printing energy balance formulation 140 may include printing energy balance formulation as an acoustic sound. As used in this disclosure, an "acoustic sound" is a vibration that propagates as an acoustic wave, through a transmission medium. Transmission medium may include type, but is not limited to, gas, liquid, solid, and the like. For example, the manufacturing device 136 may print (in another word, play) energy balance formulation as a specific music. In an embodiment, printing may include imprinting energy balance formulation 140 onto an H2 tablet. "Imprinting," as used in this disclosure is any process that impresses and/or stamps energy balance formulation 140 onto H2 tablet.

With continued reference to FIG. 1, in an embodiment, printing the energy balance formulation 140 may deposit layers of edible material or ingredient one edible material or ingredient at a time, or all edible material or ingredient at the same time, according to the determined quantity as describe above. The layers also include an exterior layer that may be either printed, sprayed on, or coated for adding that may include, but is not limited to, color, flavor, protection, additional materials or ingredients and the like. In another embodiment, printing the energy balance formulation 140 may also include printing the name and/or contents and/or instructions on the tablet and/or in addition to the tablet. Instructions may include, but is not limited to, consume amount, consume direction, consume time, warnings, restrictions, and the like. For example, the energy balance formulation may include an instruction printed on the tablet illustrating one tablet a time and three times a day. Additionally, the printing process of the energy balancing formulation 116 may occur under electrostatic field and the like.

Figure 2:
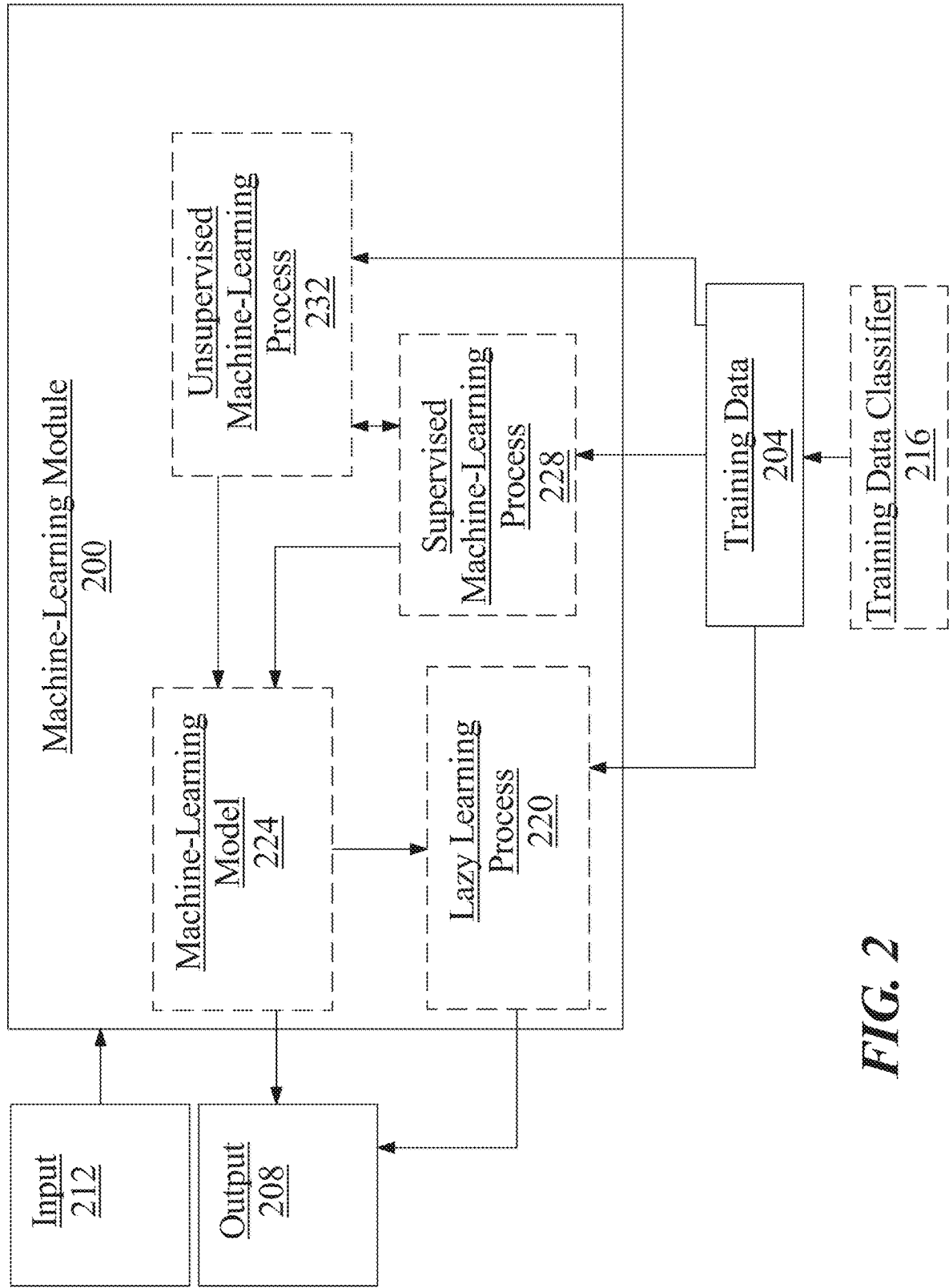
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, a machine-learning process may be trained using the energy training data where the data contains plurality energy quantifiers as input data correlate to plurality energy rebalancing plans as output data.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of energy training data to an energy rebalancing plan.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Still referring to FIG. 2 machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include one or more energy quantifier as described above as inputs, one or more energy rebalancing plans as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2 machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2 machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2 machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Referring now to FIG. 4, an exemplary embodiment of a node of a neural network is illustrated. A node may include, without limitation, a plurality of inputs xi that may receive numerical values from inputs to a neural network containing the node and/or from other nodes. Node may perform a weighted sum of inputs using weights wi that are multiplied by respective inputs xi. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights wi may be determined by training a neural network using training data, which may be performed using any suitable process as described above.

Referring now to FIG. 5, a block diagram of an exemplary embodiment of an apparatus 100 is illustrated. Apparatus 100 may include at least an applicator 504. At least an applicator 504 may include any device used to deposit layers of ingredient or material. For instance, applicator 504 may include a printer head for a 3D printer. Applicator 504 may include an extruding device for extruding fluid or paste material, a sprayer or other applicator for bonding material, an applicator for powering, a sintering device such as a laser, or other such material. Applicator 504 may draw upon one or more reservoirs of liquid, paste, and/or powdered materials, which may advance such materials to application using, without limitation, auger screws, pistons, gravity, and/or pressure.

Continuing to view FIG. 5, apparatus 100 may include a workpiece support 508. Workpiece support 508 may be a structure that supports a workpiece during the one or more manufacturing steps. Workpiece support 508 may include a base table. Base table may include a surface to which a workpiece or other components may be secured. Surface may be oriented horizontally, vertically, or in any other orientation. Surface may be substantially planar. Workpiece support 508 may include a substrate for initial deposition of material in an additive process.

Still referring to FIG. 5, apparatus 100 may include a powered additive manufacturing device 500. As used herein, a powered additive manufacturing device 500 is an additive manufacturing device 500 in which at least one component of the additive manufacturing device 500 includes at least a component powered by something other than human power. At least a component may be powered by any non-human source, including without limitation electric power generated or stored by any means, heat engines including steam, internal combustion, or diesel engines, wind power, water-power, pneumatic power, or hydraulic power. Powered components may include any components of additive manufacturing device 500. Applicator 504 may be powered; for instance, applicator 504 may include an endmill mounted on a spindle rotated by a motor (not shown). Workpiece support 508 may be powered. Where additive manufacturing device 500 is a mechanical device, motion of components along linear or rotary constraints may be powered; for instance, motion of base table along one or more linear constraints such as linear slides may be driven by a motor or other source of power. Similarly, rotation of rotary table may be driven by a power source. Tool-changer, where present, may be driven by power. In some embodiments, all or substantially all of the components of additive manufacturing device 500 are powered by something other than human power; for instance, all components may be powered by electrical power.

Further referring to FIG. 5, additive manufacturing device 500 may include an automated manufacturing system. In some embodiments, an automated manufacturing system is an additive manufacturing device 500 including a controller 512 that controls one or more manufacturing steps automatically. Controller 512 may include a sequential control device that produces a sequence of commands without feedback from other components of automated manufacturing system. Controller 512 may include a feedback control device that produces commands triggered or modified by feedback from other components. Controller 512 may perform both sequential and feedback control. In some embodiments, controller 512 includes a mechanical device. In other embodiments, controller 512 includes an electronic device. Electronic device may include digital or analog electronic components, including without limitation one or more logic circuits, such one or more logic gates, programmable elements such as field-programmable arrays, multiplexors, one or more operational amplifiers, one or more diodes, one or more transistors, one or more comparators, and one or more integrators. Electronic device may include a processor. Electronic device may include a computing device 700 as described below in reference to FIG. 7. Computing device 700 may include a computing device 700 embedded in additive manufacturing device 500; as a non-limiting example, computing device 700 may include a microcontroller 512, which may be housed in a unit that combines the other components of additive manufacturing device 500. Controller 512 may include a manufacturer client of plurality of manufacturer clients; controller 512 may be communicatively coupled to a manufacturer client of plurality of manufacturer clients.

Continue referring to FIG. 5, controller 512 may include a component embedded in additive manufacturing device 500; as a non-limiting example, controller 512 may include a microcontroller 512, which may be housed in a unit that combines the other components of additive manufacturing device 500. Further continuing the example, microcontroller 512 may have program memory, which may enable microcontroller 512 to load a program that directs additive manufacturing device 500 to perform an automated manufacturing process. Similarly, controller 512 may include any other components of a computing device 700 as described below in reference to FIG. 5 in a device housed within additive manufacturing device 500. In other embodiments, controller 512 includes a computing device 700 that is separate from the rest of the components of additive manufacturing device 500; for instance, controller 512 may include a personal computer, laptop, or workstation connected to the remainder of additive manufacturing device 500 by a wired or wireless data connection. In some embodiments, controller 512 includes both a personal computing device 700 where a user may enter instructions to generate a program for turning workpiece into a finished product, and an embedded device that receives the program from the personal computing device 700 and executes the program. Persons skilled in the art will be aware of various ways that a controller 512, which may include one or more computing device, may be connected to or incorporated in an automated manufacturing system as described above.

Still referring to FIG. 5, controller 512 may control components of automated manufacturing system; for instance, controller 512 may control elements including without limitation tool changer to switch endmills, spindle or gear systems operatively coupled to spindle to regulate spindle rotational speed, linear movement of applicator 504, base table, or both, and rotation or rotational position of rotary table. As an example, applicator 504 may be moved about using computerized numerical control (CNC) devices and/or motion controls that are automated and operate by precisely programmed commands that control movement of one or more parts of the equipment to affect the material removal. CNC machines, their operation, programming, and relation to computer aided manufacturing (CAM) tools and computer aided design (CAD) tools are well known and need not be described in detail herein for those skilled in the art to understand the scope of the present invention and how to practice it in any of its widely varying forms. Similarly, controller 512 may coordinate deposition and/or curing of material in additive manufacturing processes, where additive manufacturing device 500 is an additive manufacturing device 500. Persons skilled in the art, upon reading the entirety of this disclosure, will be aware of similar automated control systems usable for various forms manufacturing. Controller may be, be included in, include, and/or be in communication with computing device 700.

Further referencing on FIG. 5, in operation, the additive manufacturing device 500 may deposit layers of edible material or ingredient, including without limitation powdered supplements and/or substrates, as programmed by computing device 700 and/or controller 512; such programming may be driven, in turn, by energy balance formulation 140. In an embodiment, additive manufacturing device 500 may print the energy balancing formulation 116 onto the H2 tablet. As described herein, an "H2 tablet" is tablet with H2 molecular hydrogen added to it. H2 tablet may be used to reduce the production of COX-2, increase energy, slow down the aging process, and improve muscle recovery. Additionally, the printing process of the energy balancing formulation 116 may occur under electrostatic field and the like.

Referring now to FIG. 6, an exemplary method 600 for printing an energy balance formulation is illustrated. Method 600 includes a step 605, of receiving, using a processor, an energy quantifier related to a user, without limitation, as described above in reference to FIGS. 1-5. In some embodiments, the energy quantifier may be measured by examining real time by sending electric impulses with different frequency into the skin of the user. In some embodiments, the energy quantifier received at step 605 may be used to locate one or more body areas with excessive, moderate, or insufficient life energy. In some embodiments, energy quantifier may also be used to detect disorganized, misaligned, atrophied, or necrotic energy meridians of a human or life body. In some embodiments, receiving energy quantifier related to a user may include obtaining baseline energy meridian assessment and generating energy quantifier as a function of baseline energy meridian assessment. This may be implemented, as described above, in reference to FIGS. 1-5.

With continued reference to FIG. 6 method 600 includes a step 610 of training, using the processor, a machine-learning model using an energy training data wherein the energy training data contains a plurality of inputs containing energy quantifiers correlated to a plurality of outputs containing energy rebalancing plan. This may be implemented, without limitation, as described above with reference to FIGS. 1-5.

With continued reference to FIG. 6 method 600 includes a step 615 of generating, using the processor, an energy rebalancing plan wherein the energy rebalancing plan identifies an energy balance formulation. In some embodiments, the energy rebalancing plan may be generated as a function of the machine-learning model and the energy quantifier, without limitation, as described above in reference to FIGS. 1-5. In some embodiments, an energy balance formulation may also be selected as a function of the user state and target energy meridians. An energy balance formulation may include a subset of ingredients from plurality of ingredients based on the energy rebalancing plan. This may be implemented without limitation, as described above with reference to FIGS. 1-5.

With continued reference to FIG. 6 method 600 includes a step 620 of printing, using an additive manufacturing device, the energy balance formulation. In some embodiments, printing the energy balance formulation may include printing the energy balance formulation onto the H2 tablet. In some embodiments, printing the energy balance formulation may include printing the energy balance formulation as electric current. In some embodiments, printing the energy balance formulation may include printing the energy balance formulation as acoustic sound. This may be implemented without limitation, as described above with reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 620 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for printing an energy balance formulation, wherein the apparatus comprises:
   at least a processor; and
   a memory communicatively connected to the at least a processor, the memory containing instructions configuring the at least a processor to:
      receive an energy quantifier related to a user, wherein receiving the energy quantifier comprises obtaining a baseline energy meridian assessment in a specific interval;
      identify one or more body areas with insufficient life energy of the user as a function of the energy quantifier;
      generate an energy rebalancing plan as a function of the energy quantifier, wherein generating the energy rebalancing plans comprises:
         identifying an energy balance formulation, wherein the energy balance formulation comprises a dosage schedule and the memory contains instructions further configuring the at least a processor to:
            generate dosage schedule training data, wherein the dosage schedule training data comprises a plurality of inputs containing one or more ingredients and side-effects correlated to a plurality of outputs containing dosage schedules;
            train a machine-learning model using the dosage schedule training data; and
            determine the dosage schedule using the trained machine-learning model;
         identifying a quantity of the one or more ingredients in the energy balance formulation; and
         determining a probability of side effects based on the one or more ingredients of the energy balance formulation; and
      print the energy balance formulation based on the energy rebalancing plan using an additive manufacturing process, wherein printing the energy balance formulation comprises:
         transmitting the energy balance formulation to the one or more body areas with insufficient life energy of the user.

2. The apparatus of claim 1, wherein the energy quantifier comprises energy meridian flow information.

3. The apparatus of claim 1, wherein the memory contains instructions further configuring the at least a processor to identify a meridian pattern as a function of the energy quantifier.

4. The apparatus of claim 1, wherein the memory contains instructions further configuring the at least a processor to:
   generate energy training data, wherein the energy training data contains a plurality of inputs containing energy quantifiers correlated to a plurality of outputs containing energy rebalancing plans;

train a machine-learning process using the energy training data; and generate the energy rebalancing plan as a function of the trained machine-learning process and the energy quantifier.

5. The apparatus of claim 1, wherein the memory contains instructions further configuring the at least a processor to:
generate ingredient training data, wherein the ingredient training data comprises a plurality of inputs containing one or more ingredients correlated to a plurality of outputs containing one or more energy effects and interactions between ingredients;
train a machine-learning process using the ingredient training data; and
determine the quantity of the one or more ingredients using the trained machine-learning process.

6. The apparatus of claim 5, wherein the interactions between ingredients comprises negative interactions.

7. The apparatus of claim 1, wherein printing the energy balance formulation further comprises printing consumption instructions onto a tablet.

8. The apparatus of claim 1, wherein printing the energy balance formulation further comprises transmitting the energy balance formulation as an electric current.

9. A method for printing an energy balance formulation, wherein the method comprises:
receiving, using at least a processor, an energy quantifier related to a user, wherein receiving the energy quantifier comprises obtaining a baseline energy meridian assessment in a specific interval;
identifying, using the at least a processor, one or more body areas with insufficient life energy of the user as a function of the energy quantifier;
generating, using the at least a processor, an energy rebalancing plan as a function of the energy quantifier, wherein generating the energy rebalancing plans comprises:
identifying an energy balance formulation, wherein the energy balance formulation comprises a dosage schedule and the method further comprises:
generate dosage schedule training data, wherein the dosage schedule training data comprises a plurality of inputs containing one or more ingredients and side-effects correlated to a plurality of outputs containing dosage schedules;
train a machine-learning model using the dosage schedule training data; and
determine the dosage schedule using the trained machine-learning model;
identifying a quantity of the one or more ingredients in the energy balance formulation; and
determining a probability of side effects based on the one or more ingredients of the energy balance formulation; and
printing, using the at least a processor, the energy balance formulation based on the energy rebalancing plan using an additive manufacturing process, wherein printing the energy balance formulation comprises:
transmitting the energy balance formulation to the one or more body areas with insufficient life energy of the user.

10. The method of claim 9, wherein the energy quantifier comprises energy meridian flow information.

11. The method of claim 9, further comprising:
identifying, using the at least a processor, a meridian pattern as a function of the energy quantifier.

12. The method of claim 9, further comprising:
generating, using the at least a processor, energy training data, wherein the energy training data contains a plurality of inputs containing energy quantifiers correlated to a plurality of outputs containing energy rebalancing plans;
training, using the at least a processor, a machine-learning process using the energy training data; and
generating, using the at least a processor, the energy rebalancing plan as a function of the trained machine-learning process and the energy quantifier.

13. The method of claim 9, further comprising:
generating, using the at least a processor, ingredient training data, wherein the ingredient training data comprises a plurality of inputs containing one or more ingredients correlated to a plurality of outputs containing one or more energy effects and interactions between ingredients;
training, using the at least a processor, a machine-learning process using the ingredient training data; and
determining, using the at least a processor, the quantity of the one or more ingredients using the trained machine-learning process.

14. The method of claim 13, wherein the interactions between ingredients comprises negative interactions.

15. The method of claim 9, wherein printing the energy balance formulation further comprises printing consumption instructions onto a tablet.

16. The method of claim 9, wherein printing the energy balance formulation further comprises transmitting the energy balance formulation as an electric current.

* * * * *